United States Patent
Anh et al.

(10) Patent No.: US 6,947,038 B1
(45) Date of Patent: Sep. 20, 2005

(54) SYSTEMS AND METHODS FOR GENERATING AN APPLIANCE WITH TIE POINTS

(75) Inventors: Jae H. Anh, San Francisco, CA (US); Loc X. Phan, Milpitas, CA (US); Sheldon Baumrind, Berkeley, CA (US); Sean Curry, Berkeley, CA (US); Andrew Beers, Menlo Park, CA (US)

(73) Assignee: Align Technology, Inc., Santa Clara, CA (US)

(*) Notice: Subject to any disclaimer, the term of this patent is extended or adjusted under 35 U.S.C. 154(b) by 0 days.

(21) Appl. No.: 09/560,424

(22) Filed: Apr. 27, 2000

(51) Int. Cl.$^7$ ............................................... G06T 15/00
(52) U.S. Cl. ........................... 345/419; 378/168; 433/2; 433/6; 433/24
(58) Field of Search ............................. 378/9, 168–171; 433/2; 345/419

(56) References Cited

U.S. PATENT DOCUMENTS

| | | |
|---|---|---|
| 2,467,432 A | 4/1949 | Kesling |
| 3,660,900 A | 5/1972 | Andrews |
| 3,860,803 A | 1/1975 | Levine |
| 3,916,526 A | 11/1975 | Schudy |
| 3,950,851 A | 4/1976 | Bergersen |
| 4,014,096 A | 3/1977 | Dellinger |
| 4,195,046 A | 3/1980 | Kesling |
| 4,324,546 A | 4/1982 | Heitlinger et al. |
| 4,348,178 A | 9/1982 | Kurz |
| 4,478,580 A | 10/1984 | Barrut |
| 4,504,225 A | 3/1985 | Yoshii |
| 4,505,673 A | 3/1985 | Yoshii |
| 4,575,805 A | 3/1986 | Moermann et al. |
| 4,611,288 A | 9/1986 | Duret et al. |
| 4,656,860 A | 4/1987 | Orthuber et al. |
| 4,663,720 A | 5/1987 | Duret et al. |
| 4,742,464 A | 5/1988 | Duret et al. |

(Continued)

FOREIGN PATENT DOCUMENTS

| | | |
|---|---|---|
| EP | 091876 A1 | 10/1983 |
| EP | 299490 A2 | 1/1989 |
| EP | 376873 A2 | 7/1990 |
| EP | 490848 B1 | 6/1992 |
| EP | 774933 B1 | 5/1997 |
| EP | 541500 A1 | 6/1998 |
| EP | 731673 B1 | 9/1998 |
| FR | 2369828 A1 | 6/1978 |
| FR | 2652256 A1 | 3/1991 |
| WO | WO 90/08512 A1 | 8/1990 |
| WO | WO 91/04713 A1 | 4/1991 |
| WO | WO 94/10935 A1 | 5/1994 |
| WO | WO98/32394 A1 | 7/1998 |
| WO | WO 98/44865 A1 | 10/1998 |
| WO | WO 98/58596 A1 | 12/1998 |

OTHER PUBLICATIONS

Alexander et al., "The DigiGraph Work Station Part 2, Clinical Management," *JCO* (Jul. 1990), pp. 402–407.

(Continued)

*Primary Examiner*—Mark Zimmerman
*Assistant Examiner*—Lance W. Sealey
(74) *Attorney, Agent, or Firm*—Townsend and Townsend and Crew LLP

(57) ABSTRACT

Systems and methods are described for integrating anatomical information from a plurality of sources of information. The system receives two or more three dimensional (3D) anatomical maps sharing a common plane specified by three or more marker points common to the two or more maps; places one or more marker points on one or more teeth; generates a digital teeth model with the marker points; and aligns the two or more 3D anatomical maps and the teeth model using the marker points

14 Claims, 13 Drawing Sheets

U.S. PATENT DOCUMENTS

| | | |
|---|---|---|
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,837,732 A | 6/1989 | Brandestini et al. |
| 4,850,864 A | 7/1989 | Diamond |
| 4,856,991 A | 8/1989 | Breads et al. |
| 4,936,862 A | 6/1990 | Walker et al. |
| 4,937,928 A | 7/1990 | van der Zel |
| 4,964,770 A | 10/1990 | Steinbichler et al. |
| 4,975,052 A | 12/1990 | Spencer et al. |
| 4,980,905 A * | 12/1990 | Meccariello ............... 378/207 |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,128,870 A | 7/1992 | Erdman et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,496 A | 8/1995 | Andersson et al. |
| 5,447,632 A | 9/1995 | Andersson et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| 5,518,397 A | 5/1996 | Andreiko et al. |
| 5,533,895 A | 7/1996 | Andreiko et al. |
| 5,542,842 A | 8/1996 | Andreiko et al. |
| 5,549,476 A | 8/1996 | Stern |
| 5,550,891 A * | 8/1996 | Burbury et al. ............. 378/197 |
| 5,587,912 A | 12/1996 | Andersson et al. |
| 5,605,459 A | 2/1997 | Kuroda et al. |
| 5,607,305 A | 3/1997 | Andersson et al. |
| 5,645,421 A | 7/1997 | Slootsky |
| 5,655,653 A | 8/1997 | Chester |
| 5,683,243 A | 11/1997 | Andreiko et al. |
| 5,733,126 A | 3/1998 | Andersson et al. |
| 5,740,267 A | 4/1998 | Echerer et al. |
| 5,882,192 A * | 3/1999 | Bergersen ..................... 433/2 |
| 5,975,893 A | 11/1999 | Chishti et al. |
| 6,152,731 A * | 11/2000 | Jordan et al. ................ 433/69 |
| 6,158,888 A * | 12/2000 | Walker et al. .............. 378/169 |
| 6,217,334 B1 | 4/2001 | Hultgren |

OTHER PUBLICATIONS

Altschuler et al., "Laser Electro–Optic System for Rapid Three–Dimensional (3D) Topographic Mapping of Surfaces," *Optical Engineering*, vol. 20(6) (1981), pp. 953–961.

Altschuler et al., "Measuring Surfaces Space–Coded by a Laser–Projected Dot Matrix," *SPIE Imaging Applications for Automated Industrial Inspection and Assembly*, vol. 182 (1979), p. 187–191.

Altschuler et al., "Analysis of 3–D Data for Comparative 3–D Serial Growth Pattern Studies of Oral–Facial Structures," Program and Abstracts of Papers, Feb. 1975, *Journal of Dental Research*, vol. 54, IADR Abstracts 1979, 2 pages total.

Altschuler, "3D Mapping of Maxillo–Facial Prosthesis," AADR Abstract #607, 1980, 2 pages total..

American Association for Dental Research, Summary of Activities, Mar. 20–23, 1980, Los Angeles, CA, p. 195.

Andersson et al., "Clinical Results with Titanium Crowns Fabricated with Machine Duplication and Spark Erosion," *Acta Odontological Scandinavia*, vol. 47 (1989), pp. 279–286.

Baumrind et al., "A stereophotogrammetric system for the detection of prosthesis loosening in total hip arthroplasty, Applications of Human Biostereometrics (NATO)," Proceedings of the Society of Photo–Optical Instrumentation Engineers, vol. 166, Jul. 9–13, 1978, pp. 112–123.

Baumrind et al., Mapping the Skull in 3–D, Reprinted from The Journal, *California Dental Association*, vol. 48, No. 2 (1972 Fall Issue) 11 pages total.

Baumrind et al., "Seminars in Orthodontics," *Seminars in Orthodontics*, vol. 7, No. 4 (Dec. 2001), p. 222.

Baumrind, "A System for Craniofacial Mapping Through the Integration of Data from Stereo X–Ray Films and Stereo Photographs," An invited paper submitted to the 1975 American Society of Photogram. Symposium on Close–Range Photogram. Systems, University of Ill. Aug. 26–30, 1975, pp. 1–25.

Baumrind, "Integrated Three–Dimensional Craniofacial Mapping: Background, Principles, and Perspectives," *Seminars in Orthodontics*, vol. 7, No. 4 (Dec. 2001), pp. 223–232.

Begole et al., "A Computer System for the Analysis of Dental Casts," *The Angle Orthodontist*, vol. 51 No. 3 (Jul. 1981), pp. 253–259.

Bernard et al., "Computerized diagnosis in Orthodontics for Epidemiological Studies" (progress report), Abstracts of Papers, *Journal of Dental Research;* vol. 71, Special Issue Mar. 1–14, 1992, pp. 28–36.

Bhatia et al., "A Computer–Aided Design for Orthognathic Surgery," *British Journal of Oral and Maxillofacial Surgery*, vol. 22 (1984), pp. 237–253.

Biggerstaff et al., "Computerized analysis of occlusion in the postcanine dentition," *American Journal of Orthodontics*, vol. 61, No. 3 (Mar. 1972), pp. 245–254.

Biggerstaff, "Computerized Diagnostic Setups and Simulations," *The Angle Orthodontist*, vol. 40, No. 1 (Jan. 1970), pp. 28–36.

Brandestini et al., "Computer Machined Ceramic Inlays: In Vitro Marginal Adaptation," *Journal of Dental Research*, vol. 64/Special Issue/Abstracts, IADR/AADR Abstracts 1985, 1 page total.

Brook et al., An Image Analysis System for the Determination of Tooth Dimensions from Study Casts: Comparison with Manual Measurements of Mesio–distal Diameter, Abstract of Papers, 1985, Dept. of Children's Dentistry and Orthodontics, *J Dent Res.*, Mar. 1986, pp. 428–431.

Burstone (interview), "Dr. Charles J. Burstone on The Uses of the Computer in Orthodontic Practice (Parts 1 and 2)," *Journal of Clinical Orthodontics*, (Part 1) vol. 8, No. 7 , Jul. 1979; (Part 2) vol. 8, No. 8 pp. 539–551, Aug. 1979.

Burstone et al., "Precision adjustment of the transpalatal lingual arch: Computer arch form predetermination," *Am. Journal of Orthodontics,* vol. 79, No. 2 (Feb. 1981), pp. 115–133.

Chaconas et al., "The DigiGraph Work Station, Part 1, Basic Concepts," *JCO* (Jun. 1990), pp. 360–367.

Chafetz et al., "Subsidence of the Femoral Prosthesis, A Stereophotogrammetric Evaluation," *Clinical Orthopaedics and Related Research,* No. 201 (Dec. 1985), pp. 60–67.

Chiappone, "Constructing the gnathologic setup and positioner" *J. Clin. Orthod.,* 14:121–133, 1980.

Cottingham, "Gnathologic clear plastic positioner" *Am. J. Orthod.,* 55:23–31, 1969.

Crawford, "Computers in Dentistry: Part 1: CAD/CAM: The Computer Moves Chairside," "Part 2: F. Duret—A Man With A Vision," "Part 3: The Computer Gives New Vision—Literally," "Part 4: Bytes 'N Bites" The Computer Moves From The Front Desk To The Operatory, *Canadian Dental Journal,* vol. 54(9), , (1988), pp. 661–666.

Crawford, "CAD/CAM in the Dental Office: Does It Work?" *Canadian Dental Journal,* vol. 57, No. 2 (Feb. 1991), pp. 121–123.

Crooks, "CAD/CAM Comes to USC," *USC Dentistry,* (Spring 1990) pp. 14–17.

Cureton, "Correcting malaligned mandibular incisors with removable retainers" *J. Clin. Orthod.,* 30:390–395, 1996.

Curry et al., "Integrated Three–Dimensional Craniofacial Mapping at the Craniofacial Research Instrumentation Laboratory/University of the Pacific," *Seminars in Orthodontics,* vol. 7, No. 4 (Dec. 2001), pp. 258–265.

Cutting et al., "Three–Dimensional Computer–Assisted Design of Craniofacial Surgical Procedures: Optimization and Interaction with Cephalometric and CT–Based Models," *Plastic and Reconstructive Surgery,* vol. 77, No.: 6 (Jun. 1986), pp. 877–885.

DCS Dental AG, "The CAD/CAM 'DCS Titan System' for Production of Crowns/Bridges" *DSC Production AG,* Jan. 1992, pp. 1–7.

DeFranco et al., "Three–Dimensional Large Displacement Analysis of Orthodontic Appliances," *J. Biomechanics,* vol. 9 (1976), pp. 793–801.

Dental Institute University of Zurich Switzerland, Program for International Symposium on Computer Restorations: State of the Art of the CEREC–Method, May 1991, 3 pages total.

DenTrac Corporation, Dentrac document, pp. 4–13.

Duret et al, "CAD–CAM in Dentistry," *Journal of the American Dental Association,* vol. 117 (Nov. 1988), pp. 715–720.

Duret et al., "CAD/CAM imaging in dentistry," *Current Opinion in Dentistry,* vol. 1 (1991), pp. 150–154.

Duret, "The Dental CAD/CAM, General Description of the Project," *Hennson International Product Brochure,* Jan. 1986., 18 pages total.

Duret, "Vers une prosthese informatisee," (English translation also attached), *Tonus,* vol. 75, (Nov. 15, 1985), pp. 55–57.

Economides, "The Microcomputer in the Orthodontic Office," *JCO,* (Nov. 1979), pp. 767–772.

Elsasser, "Some observations on the history and uses of the Kesling positioner" *Am. J. Orthod.,* 36:368–374, 1950.

Faber et al., "Computerized interactive orthodontic treatment planning," *Am. J. Orthod.,* vol. 73, No. 1 (Jan. 1978), pp. 36–46.

Felton et al. "A computerized analysis of the shape and stability of mandibular arch form," *Am. Journal of Orthodontics and Dentofacial Orthopedics,* vol. 92, No. 6 (Dec. 1987), pp. 478–483.

Friede et al., "Accuracy of Cephalometric Prediction in Orthognathic Surgery,"Abstract of Papers, *Journal of Dental Research,* vol. 70 (1987), pp. 754–760.

Gim–Alldent Deutschland, "Das DUX System: Die Technik" 4 pages total.

Grayson, "New Methods for Three Dimensional Analysis of Craniofacial Deformity," Symposium: Computerized Facial Imaging in Oral and Maxilofacial Surgery, AAOMS Sep. 13, 1990, 3 pages total.

Guess et al., "Computer Treatment Estimates in Orthodontics and Orthognathic Surgery," *JCO,* (Apr., 1989), pp. 262–228.

Heaven et al., "Computer–based Image Analysis of Artificial Root Surface Caries,""Automated Identification of Landmarks in Cephalometric Radiographs," Abstracts of Papers, *Journal of Dental Research,* vol. 67, Mar. 9–13, 1988, 2 pages total.

Hoffmann et al., "Role of Cephalometry for Planning of Jaw Orthopedics and Jaw Surgery Procedures," (Article Summary in English, article in German), *Informationen,* (Mar. 1991), pp. 375–396.

Huckins, "CAD–CAM Generated Mandibular Model Prototype from MRI Data," *AAOMS* 1999, p. 96.

Inside the ADA, *Journal Of The American Dental Assoc.,* vol. 118 (Mar. 1989) 9 pages total.

JCO Interviews, "Craig Andreiko , DDS, MS on the Elan and Orthos Systems", JCO, (Aug. 1994), pp. 459–468.

JCO Interviews, "Dr. Homer W. Phillips on Computers in Orthodontic Practice, Part 2," JCO, (Dec. 1983), pp. 819–831.

Jerrold, "The problem, electronic data transmission and the law," *AJO–DO,* (Apr. 1988), pp. 478–479.

Jones et al., "An Assessment of the Fit of a Parabolic Curve to Pre– and Post–Treatment Dental Arches," *British Journal of Orthodontics,* vol. 16 (1989), pp. 85–93.

Kamada et al., "Case reports on tooth positioners using LTV vinyl silicone rubber" J. Nihon University School of Dentistry, 26(1):11–29, 1984.

Kamada et al., "Construction of tooth positioners with LTV vinyl silicone rubber and some case reports" J. Nihon University School of Dentistry, 24(1):1–27, 1982.

Kanazawa et al., "Three–Dimensional Measurements of the Occlusal Surfaces of Upper Molars in a Dutch Population," *J. Dent Res. ,* vol. 63, No. 11 (Nov. 1984), pp. 1298–1301.

Kesling, "Coordinating the predetermined pattern and tooth positioner with conventional treatment" *Am. J. Orthod. Surg.,* 32:285–293, 1946.

Kesling, "The philosophy of the tooth positioning appliance" *Am. J. Orthod. Oral. Surg.,* 31(6):297–304, 1945.

Kleemann et al., "The speed positioner" *J. Clin. Orthod.,* 30:673–680, 1996.

Kuroda et al., "Three–dimensional dental cast analyzing system using laser scanning" *Am. J. Orthod. Dentofac. Orthop.,* 110:365–369, 1996.

Laurendeau et al., "A Computer–Vision Technique for the Acquisition and Processing of 3–D Profiles of Dental Imprints: An Application in Orthodontics," *IEEE Transactions on Medical Imaging,* vol. 10, No. 3 (Sep. 1991), pp. 453–461.

Leinfelder et al., "A new method for generating ceramic restorations: a CAD–CAM system," *Journal Of The American Dental Assoc.,* vol. 118, No. 6 (Jun. 1989), pp. 703–707.

McNamara et al., *Orthodontic and Orthopedic Treatment in the Mixed Dentition,* Needham Press, Jan. 1993. pp. 347–353.

McNamara et al., "Invisible Retainers," *J. Clinical Orthodontics,* (Aug. 1985) pp. 570–578.

Moermann et al., "Computer Machined Adhesive Porcelain Inlays: Margin Adaptation after Fatigue Stress," IADR Abstract 339, *Journal of Dental Research,* vol. 66(a) (1987), p. 339.

Mörmann et al., "Marginal Adaptation von adhasiven Porzellaninlays in vitro, "*Schwizerische Monatsshrift fur Zahnmedizin,* vol. 85 (1985), p. 1118–1129.

Mörmann et al., "Marginale Adaptation von adhäsuven Porzellaninlays in vitro," Separatdruck aus: Schweiz. Mschr. Zahnmed. 95: 1118, 1985.

Nahoum, "The vacuum formed dental contour appliance" *The New York State Dental Journal,* 30(9):385–390, Nov. 1964.

Nash, "CEREC CAD/CAM Inlays: Aesthetics and Durability in a Single Appointment," *Dentistry Today,* (Oct. 1990), pp. 20, 22–23, 54.

Nishiyama et al., "A new construction of tooth repositioner by LTV vinyl silicone rubber" J. Nihon University School of Dentistry, 19(2):93–102, 1977.

Pinkham, "'Foolish' Concept Propels Technology," *Dentist,* Jan./Feb. 1989, 3 pages total.

Pinkham, "Inventor's CAD/CAM may transform dentistry," *Dentist,* Sep. 1990, 3 pages total.

Ponitz, Invisible Retainers, 59 *Am. J. Orthodontics,* Mar. 1971, pp. 266–272.

Procera Research Projects, *PROCERA Research Projects* 1993—Abstract Collection, 1993, pp. 3–28.

Rekow, "A Review of the Developments in Dental CAD/CAM Systems," (contains references to Japanese efforts and content of the papers of particular interest to the clinician are indicated with a one–line summary of their content in the bibliography), Dental Clinics: *Prosthodontics and Endodontics,* pp. 25–33, 1992.

Rekow, "CAD/CAM in Dentistry: A Historical Perspective and View of the Future," *Journal,* vol. 58 No. 4, (Apr, 1992), pp. 283, 287–288.

Rekow, "Computer–Aided Design and Manufacturing In Dentistry: A Review of the State of the Art," *The Journal of Prosthetic Dentistry,* vol. 58, No. 4 (Oct. 1987), pp. 512–516.

Rekow, "Dental CAD–CAM Systems: What is the State of the Art?" *Journal of the American Dental Assoc.,* vol. 122 (1991), pp. 43–48.

Rekow, "Feasibility of an Automated System for Production of Dental Restorations," PhD Thesis, Univ. of Minnesota, Nov. 1988, 244 pages total.

Richmond et al., Research Reports, "The development of a 3D Cast Analysis System," *British Journal of Orthodontics,* pp. 53–54.

Richmond, "Recording the dental cast in three dimensions," *Am. J. Orthod. Dentofac. Orthop.,* vol. 92, No. 3, (Sep. 1987), pp. 199–206.

Rudge, "Dental arch analysis: arch form, A review of the literature," *European Journal of Orthodontics,* vol. 3, No. 4 (1981), pp. 279–284.

Sakuda et al., "Integrated information–processing system in clinical orthodontics: An approach with use of a computer network system," *Am. J. Orthod. Dentofac. Orthop.* vol. 101 No. 3 (Mar. 1992), pp. 210–220.

Schellhas et al., "Three–Dimensional Computer Tomography in Maxillofacial Surgical Planning," *Arch Otolamgol Head Neck Surg.* vol. 114 (Apr. 1988), pp. 438–442.

Segu et al., "Computer–aided Cefalometry and New Mechanics in Orthodontic" (Article Summary in English, article in German), *Fortschr. Kieferorthop.* 44, 370–376 (Nr. 5), 1983.

Shilliday, "Minimizing finishing problems with the mini–positioner" *Am. J. Orthod.* 59:596–599, 1971.

Siemens, "CEREC—Computer–Reconstruction, "High Tech in der Zahnmedizin, 14 page total.

Sirona Dental Systems GmbH, CEREC 3D, Manuel utilisateur, Version 2.0X (in French), 2003, 114 pages total.

Stoll et al., "Computer–aided Technologies in Dentistry" (Article Summary in English, article in German), *Dtsch Zahnärztl Z* 45, 314–322, 1990.

U.S. Department of Commerce, National Technical Information Service, "Automated Crown Replication Using Solid Photography SM," Solid Photography Inc. Melville NY, Oct. 1977, 21 pages total.

U.S. Department of Commerce, National Technical Information Service, "Holodontography: An Introduction to Dental Laser Holography," School of Aerospace Medicine Brooks AFB Tex, Mar. 1973, 37 pages total.

U.S. Appl. No. 60/050,342, filed on Jun. 20, 1997, 41 pages total.

Van der Linden et al., Three–Dimensional Analysis of Dental Casts by Means of the Optocom, *J Dent Res,* Jul.–Aug. 1972, p. 1101.

Van der Linden, "A New Method to Determine Tooth Positions and Dental Arch Dimensions," Jul.–Aug. 1972, p. 1104.

Van der Zel, "Ceramic–fused–to–metal Restorations with a New CAD/CAM System," *Quintessence International,* vol. 24(11) (1993), pp. 769–778.

Várady et al., "Reverse Engineering of Geometric Models—An Introduction," May 13, 1996, pp. 1–28.

Warunek et al., "Clinical use of silicone elastomer appliances," *JCO,* MH (10):694–700, 1989.

Warunek et al., "Physical and mechanical properties of elastomers in orthodontic positioners" *Am. J. Orthod. Dentofac. Orthop.,* 95:388–400, 1989.

Wells, "Application of the positioner appliance in orthodontic treatment" *Am. J. Orthodont.,* 58:351–366, 1970.

Williams, "Dentistry and CAD/CAM: Another French Revolution, " *Journal of Dental Practice Admin.,* Jan./Mar. 1987, pp. 2–5.

Williams, "The Switzerland and Minnesota Developments in CAD/CAM," *Journal of Dental Practice Admin.,* pp. 50–55, Apr./Jun. 1987.

Wishan, "New Advances in Personal Computer Applications for Cephalometric Analysis, Growth Prediction, Surgical Treatment Planning and Imaging Processing, "Symposium: Computerized Facial Imaging in Oral and Maxilofacial Surgery, AAOMS, Sep. 13, 1990, p. 5.

Yamamoto et al., "Three–Dimensional Measurement of Dental Cast Profiles and Its Applications to Orthodontics," Annual Int'l Conf. of IEEE Engineering in Medicine and Biology Society, vol. 12, No. 5, pp. 2051–2053, 1990.

Yamamoto et al., "Optical measurement of dental cast profile and application to analysis of three-dimensional tooth movement in orthodontics," *Frontiers in Med. and Biol. Eng'g,* vol. 1, No. 2 (1988), pp. 119–130.

Doyle, "Digital Dentistry" *Computer Graphics World* (Oct. 2000) pp. 50–52, 54.

Redmond et al., "Clinical Implications of Digital Orthodontics" *Am. J. Orthodont. Dentofacial Orthopedics* (2000) 117(2):240–242.

\* cited by examiner

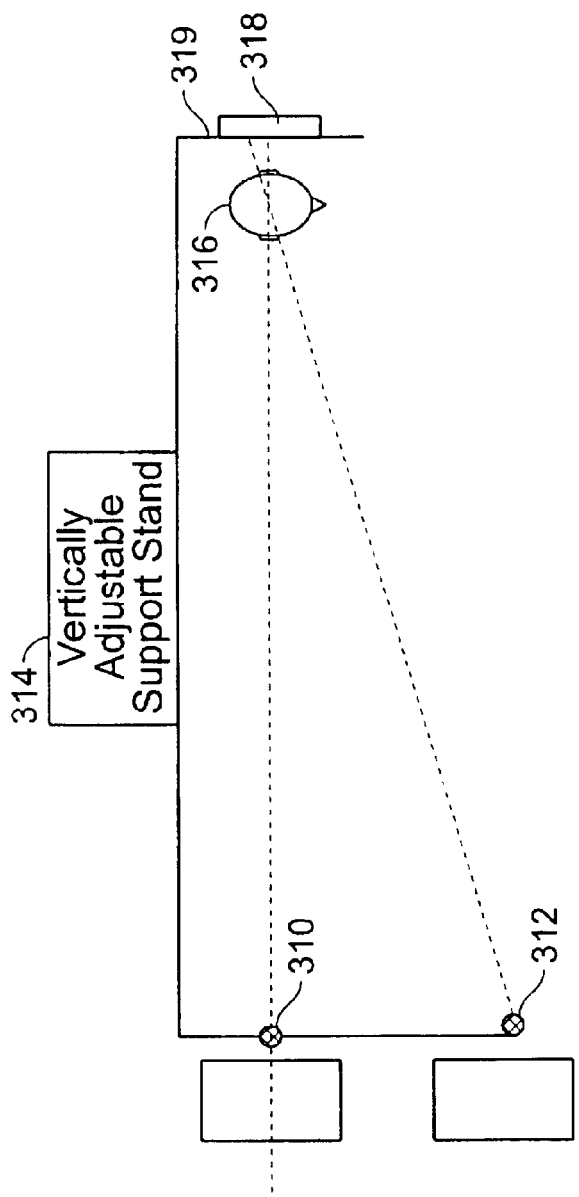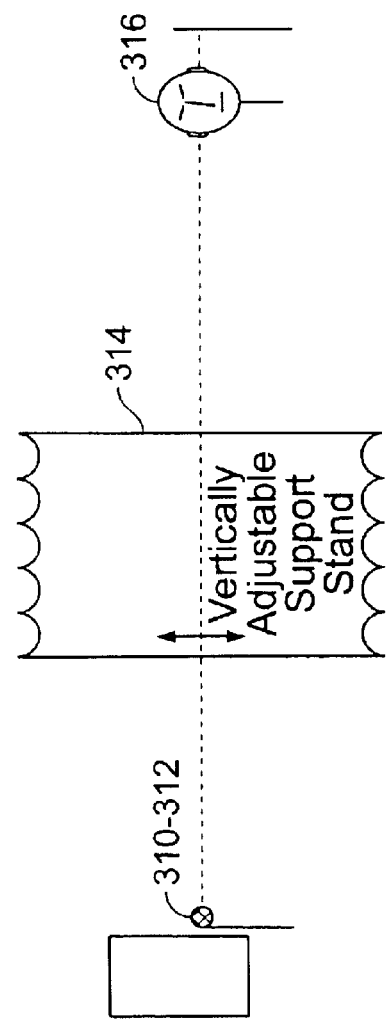

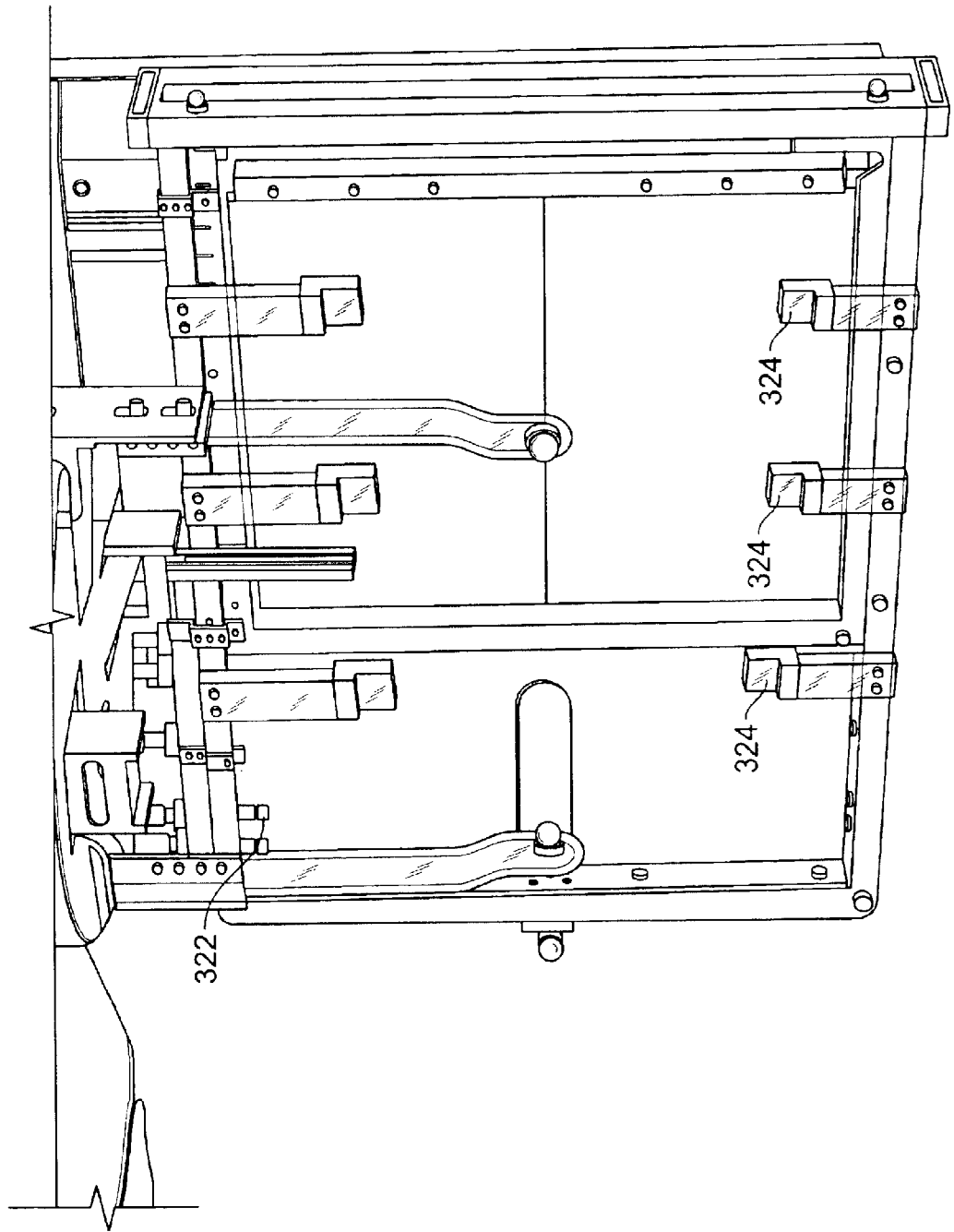

SYSTEMS AND METHODS FOR GENERATING AN APPLIANCE WITH TIE POINTS

This application is related to U.S. patent application Ser. No. 09/560,052 entitled "Systems and Methods for Integrating 3D Diagnostic Data." The present invention relates to three-dimensional (3D) representations of objects such as anatomical structures.

BACKGROUND

Many applications, including medical and dental applications, rely on data visualization to provide a holistic display of information and to maximize the amount of information that can be conveyed at once. In data visualization, a graphical mapping from an information space to a display space is performed. The process allows a user to visually explore the 3D representations or models of objects. The 3D models become much more useful when they are integrated, that is, when a number of related models are merged and overlaid to provide spatial context, among others.

For example, knowledge of the spatial relationships of the jaws, teeth and cranium is needed in various dental applications. Such relationships include the relative positions of hard structures (teeth and bones) and overlying soft tissues and skin. The customary types of physical record obtained by dental clinicians include photographs of the face (both extra-oral and intra-oral), X-ray images of the skull taken from different projections, and plaster study casts of the teeth themselves. Conventionally, most diagnoses are currently made using 2D photographs, 2D X-ray films and 3D plaster study casts.

SUMMARY

A system integrates anatomical information from a plurality of sources of information. The system receives two or more three dimensional (3D) anatomical maps sharing a common plane specified by three or more marker points common to the two or more maps; places one or more marker points on one or more teeth; generates a digital teeth model with the marker points; and aligns the two or more 3D anatomical maps and the teeth model using the marker points.

Implementations of the system may include one or more of the following. The anatomical information can be stereo craniofacial data. One of the anatomical maps is an X-ray map. The X-ray map is generated using correlated points on X-ray pairs and using y-parallax measurements. The X-ray information is stereo. The system can calibrate one or more X-ray sources. The calibration determines a principal distance from an X-ray source to a film plane. The system can also characterize internal dimensions of the one or more X-ray sources by locating an X-ray film relative to an X-ray source. One of the anatomical map can be a 3D image map. Another anatomical map can be a dental map. Each marker can be a tie point. The system can also use discrete anatomical landmark information. The system can display the aligned maps as an integrated 3D anatomical model.

In another aspect, a method visualizes anatomical information from a plurality of sources by receiving X-ray information having X-ray marker information; receiving a three-dimensional anatomical information having anatomical marker information; receiving a three-dimensional teeth model having teeth marker information; aligning the X-ray information, 3D anatomical information, and the 3D teeth model using the marker information; and displaying the aligned X-ray information, 3D anatomical information, and the 3D teeth model.

In another aspect, a system includes an appliance with one or more teeth markers embedded therein; an X-ray camera receiving X-ray information with X-ray marker information; a three-dimensional digital camera receiving three-dimensional anatomical information with anatomical marker information; a dental scanner to generate a three-dimensional teeth model with teeth marker information; a computer to align the X-ray information, 3D anatomical information, and the 3D teeth model using the marker information.

Advantages of the invention may include one or more of the following. The system improves the capability of orthodontic practitioners to develop diagnoses orthodontic treatment plans.

Through the use of markers called tie points, the system allows merging of multiple data sources such as X-ray images, study cast images or models, and facial images into a single unified coordinate system. Because the coordinate frame of reference is unified, two or more data sources that are not directly tied together can in fact be compared. For example, because the study casts are referred to the X-ray anatomic framework, and the facial imagery is tied to the same X-ray anatomic framework, therefore the study casts and facial imagery can be compared to each other, even though they are not directly tied to each other. Overall, the system also provides a uniform accurate coordinate system in three dimensions, meaning that accurate unbiased measurements can be obtained, regardless of subject orientation.

The system permits each type of anatomical structure to be imaged using an appropriate imaging modality and perspective best suited for locating that structure, after which all the optimal locations can be merged into a common 3D map by using tie points. The system is robust in construction, simple to operate and requires a minimum departure from the technician's usual procedures. The user only needs to identify and locate landmarks, after which all measurements, computations, and integrations of data from different primary sources are made semi-automatically or automatically by computers and computer-aided technicians.

The ability to tie the data sources together opens up new diagnostic and treatment planning opportunities. The system supports a dynamic analysis of the functioning of the jaws, teeth, and musculature.

BRIEF DESCRIPTION OF THE DRAWINGS

FIGS. 3A, 3B and 3C illustrate top view, front view and perspective view of an embodiment of a stereo X-ray machine.

FIGS. 5A–5B shows a cassette carrier or holder.

DESCRIPTION

Figure 1:
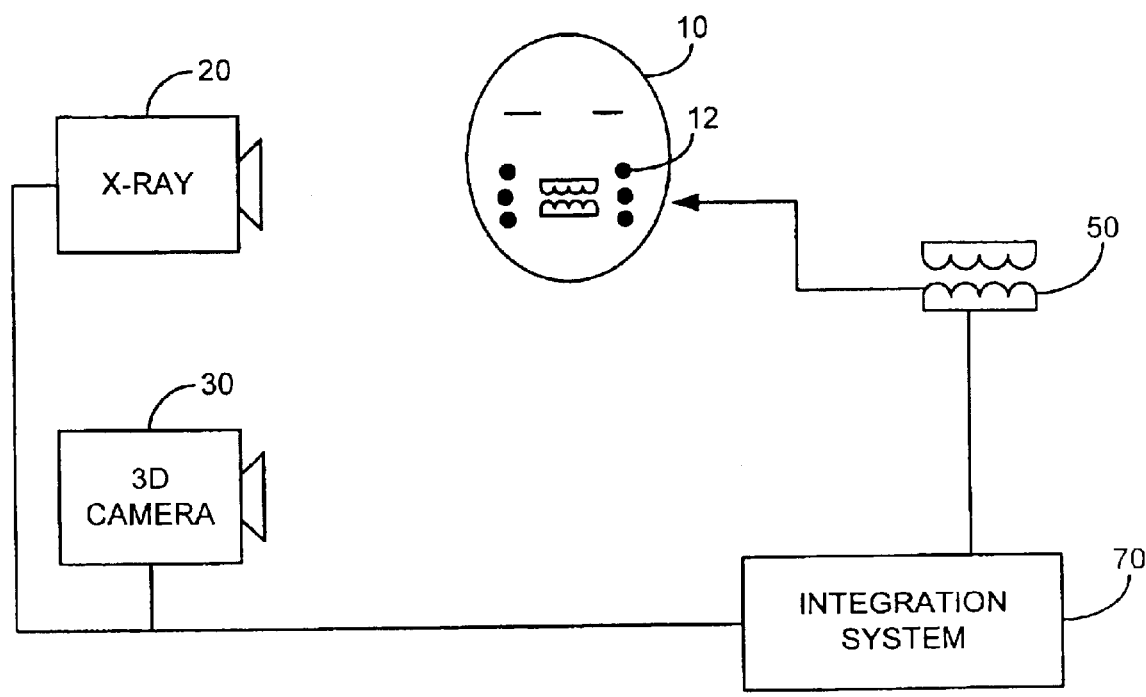
FIG. 1 is a diagram showing a system for performing integrated three-dimensional craniofacial analysis from a combination of data sources

FIG. 1 shows a system that enables digitally encoded graphic representations the teeth and the facial surface to be merged with accuracy and precision, making possible three dimensional diagnosis, treatment planning, and evaluation of results in orthodontics and other types of dental and craniofacial treatment.

Referring now to FIG. 1, a set of radiopaque and photographically visible spherical tie points 12 are temporarily mounted on the surfaces of the face and teeth of a patient 10. With these tie points 12 in position, two or more skull X-ray images are generated from different perspectives using an X-ray camera 20. The camera 20 can be a stereo camera with two X-ray emitters, or can be a calibrated single emitter system. The X-ray images can utilize either coplanar or biplanar geometry. Each tie point 12 is unambiguously visible on two or more radiographic projections. The spatial relationships between the X-ray emitter(s) and the X-ray film or other image-capture medium are also known with accuracy and precision. The X-ray camera 20 is calibrated with a specialized calibration apparatus and associated software. The X-ray camera 20 uses a cassette-holder installed at the opposite end of the X-ray camera from the X-ray tube.

The skull X-ray images can be of either the bi-planar or co-planar type. If they are of the coplanar type, three-dimensional locations of structures not lying in the sagittal plane can be obtained. Thus, 3D wire frame representations of skull and jaw anatomy can be constructed in a manner similar to the 2D tracings of traditional orthodontic cephalometrics.

A 3D image-capture system 30 captures digital 3D images of both 1) the tooth surfaces and their associated tie points and 2) the facial surface and its associated tie points. Particularly, three or more measurable tie points are available in common for each pair of 3D images to be integrated or merged.

Additionally, an appliance 50 is mounted on the patient's teeth. In one of these implementations, the tooth tie points are temporarily cemented to the teeth prior to taking the impression for the appliance 50. In the other implementation, the impression is taken first and the tie points are incorporated into the appliance 50 during its fabrication. An integration system 70 receives data from the X-ray camera 20, the 3D camera 30 and a digital model of the appliance 50 and integrates the data to provide a holistic view of the patient 10 for treatment. The integration system 70 is shown in more detail in FIG. 10.

An exemplary use of the system of FIG. 1 is discussed next. First, the physical patient records are acquired. During this process, a treating professional such as an orthodontist or otherwise secures four to six bonds radiopaque metal spheres to upper canines and molars and four radiopaque metal spheres to lower canines and molars. The metal markers are called "tie points" such as are shown in FIGS. 6–8B. They will later be used for linking data from images of different types into a common three-dimensional coordinate system. High quality upper and lower impressions are then taken, suitable for destructive scanning, for example. Additional tie points, like the one in FIG. 7, are attached to the facial surface prior to taking X-rays and facial photographs in a configuration similar to that shown in FIG. 9. Lateral and frontal stereo X-ray images and a single panoramic X-ray image are taken with the tie points in place, using a suitable digital or analog X-ray system. Frontal and lateral 3D facial photographs are taken using a 3D photographic system. Fully digital versions of all the above records are stored in the integration system 70.

In order to integrate the data from all sources the positions of the tie points on each physical record must be located. On study casts such as those made in accordance with U.S. Pat. No. 5,975,893 issued to Align Technology, Inc., the 3D data are generated by the Align software/hardware system. On the facial photographs, the procedure can be done by an operator on screen, also directly in three dimensions using a suitable 3D camera. The reconstruction of X-ray information on tie point locations must be done individually on each image as an on-screen operation. However, it can be done by a minimally trained technician or assistant and does not require any orthodontist's time. Automated digital pattern recognition methods may also be used to locate tie points on images without human intervention.

For the three space coordinates of an anatomical landmark on an X-ray cephalogram to be precisely known, the landmark must be independently located on both images of an X-ray stereo pair. This step requires involvement of either an orthodontist or a trained technician or dental assistant. Since the tie points are in the same position as the face during the taking of both the lateral X-ray images and the frontal X-ray images, all anatomical landmarks can be methodically transferred and displayed in the proper anatomic relationship to each other. The existence of the tie points allows landmark information from lateral images to be precisely related to information from frontal images despite changes in position of the head between stereo pairs. In addition, when information from a panoramic X-ray image is combined with information from the study cast map, the positions of tooth roots will be able to be located with only slightly reduced accuracy and precision.

At this point, the treating professional has available a fully explorable multi-layered representation of the skull in three dimensions. Measurements from the teeth to each other and to the surfaces of the face can be performed using a mouse-driven cursor. If the treating professional desires conventional two dimensional cephalometric information, he or she can obtain it by locating landmarks and surfaces solely on the centered lateral and centered frontal images from the emitter 310 without the emitter 312 (FIGS. 3A–3B). In order to obtain full skeletal information in three dimensions, the treating professional or a trained assistant will be required to locate the same landmark on each of two stereo X-ray images using the emitters 310–312.

In one implementation, to assist in relating the data from the data sources, radiopaque and photographable metal spheres are attached to the surface of the face while similar spheres are mounted on temporary removable plastic templates which are formed on the study casts and are readily transferable between the casts and the mouth. All these reference markers are mounted on the face or in the mouth at the time the appropriate stereo X-ray pairs are exposed. Following processing of the images, the tie points coordinates are located and mapped in a fashion identical to that employed for any anatomical landmark of interest. Landmark locations on the final maps are usually expressed in terms of an anatomical coordinate system based on the lateral skull X-ray film map. After the various individual coordinate maps for the X-ray films, study casts, and facial photography have been generated, they are integrated with each other through a series of mathematical transformations. After these transformations, the resulting integrated map can be visualized, manipulated and measured on a computer monitor.

Figure 2:
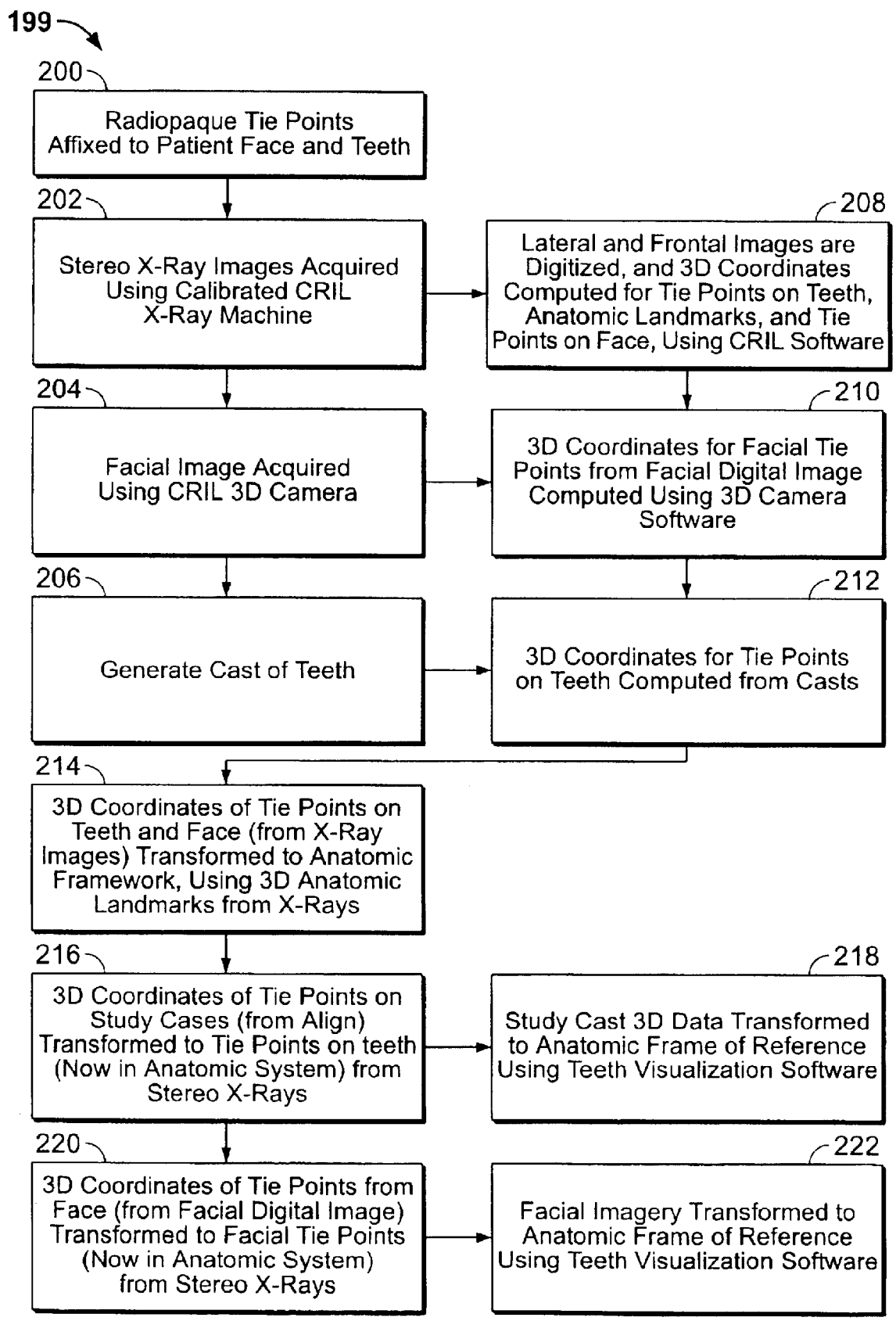
FIG. 2 shows the sequence of processes by which integrated 3D graphical and numerical data are generated for storage, recovery and utilization by the database shown in FIG. 1.

The information stored in the integration system 70 is merged to create a holistic view of the patient data from a plurality of data sources. FIG. 2 shows a process 199 which uses information from the raw data acquisition module and database. First, an appliance containing radiopaque tie points or markers is created. The tie points are identifiable markers that are visible in multiple types of images, or across multiple time points within a single type of image. The locations of the markers are specified in advance. When digital camera 3D data is merged with stereo X-ray data, common points in both sets of images are needed. In this case, small radiopaque spheres are temporarily placed on the face of the patient. They show up as small "targets" in the digital facial images. Because they are radiopaque, they also show up in the X-rays. Then 3D coordinates are computed for these common tie points from both the stereo X-rays and from the digital facial photographs. Once the coordinates are known from both sources, a mathematical transformation can be applied to rotate and translate the facial data into the same frame of reference as the X-ray data.

In the process 199, the radiopaque markers are then positioned on the patient's teeth at their designated locations using the aligner (step 200). At the same time, the patient is also fitted with a second series of tie points that consists of radiopaque markers on the face. Next, stereo X-ray images are acquired using a calibrated X-ray machine (step 202). Lateral and frontal images are digitized, and three dimensional coordinates are computed for the tie points on the teeth, the tie points on the face, and any desired anatomical landmarks visible on any two or more X-ray images (step 208).

From step 202, 3D facial data are acquired using a 3D camera (step 204). Next, 3D coordinates for facial Tie Points from facial digital image are computed (step 210). From step 204, one or more casts are created (step 206), and 3D coordinates for tie points on teeth computed from the casts (step 212). The 3D coordinates are computed from the study casts for the tie points on the teeth. At this point, 3D coordinates are available for: a) anatomical features from X-rays; b) tie points on the teeth from X-rays; c) tie points on the face from X-rays and facial images; e) tie points on the study cast and therefore the model of the dentition.

During this process, the correspondences between the markers on the teeth and their images on the X-ray images are identified. Also, the correspondences between the markers on the face and the images of the markers on the X-ray images are identified. Using the two pairs of correspondences, the three data sets are mathematically registered in 3D space as a computer operation so that the corresponding tie points coincide. The integrated map can now be viewed in any desired orientation.

Once aligned, the system can display all three data sets together with the upper and lower tooth images. The face image is correctly positioned with respect to the X-ray image. The stereo X-ray and the resulting anatomical coordinates act as a framework or scaffold upon which the other data sources (study cast and facial images) are hung. In this way, the study cast data and the facial image data can be visually and analytically compared to each other, even though there is no direct data connection between the two.

3D coordinates of tie points on the patient's teeth and face (from X-ray Images) are transformed to an anatomical framework (step 214). Further, 3D Coordinates of Tie Points on the study casts are transformed to the teeth tie points from the stereo X-rays (step 216). From step 216, the study cast 3D data is transformed to the anatomic frame of reference using visualization software (218).

From step 216, 3D coordinates of tie points from the patient's face (from facial digital images) are transformed to the facial tie points (now in the anatomical frame of reference) from stereo X-rays (step 220). From step 220, the facial imagery is transformed to the anatomic frame of reference using visualization software (222).

In sum, two appliances representative of the two jaws are fabricated upon the study casts of the upper and lower dental arches in such a manner that the teeth can occlude freely and without interference with the appliances in place. Each appliance has fastened to its surface three or more radiopaque metal markers called tie points. The same technique is used on the facial 3D photos to define a known plane in the face by the expedient of placing three or more radiopaque and photographable markers (tie points) on its exterior surface. The stereo X-rays of the skull are made with the appliances in place in the mouth and with the facial tie points in position. Because of the radiopaque property of the tie points, they will also be unambiguously identifiable in the stereo X-rays of the skull.

Figure 6:
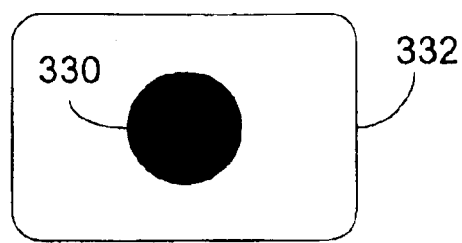
FIG. 6 shows two views of a tie point fitting which a clinician can bond (attach) directly to a tooth.
Figure 6:
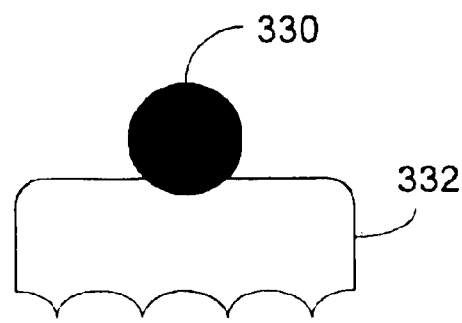
Figure 7:
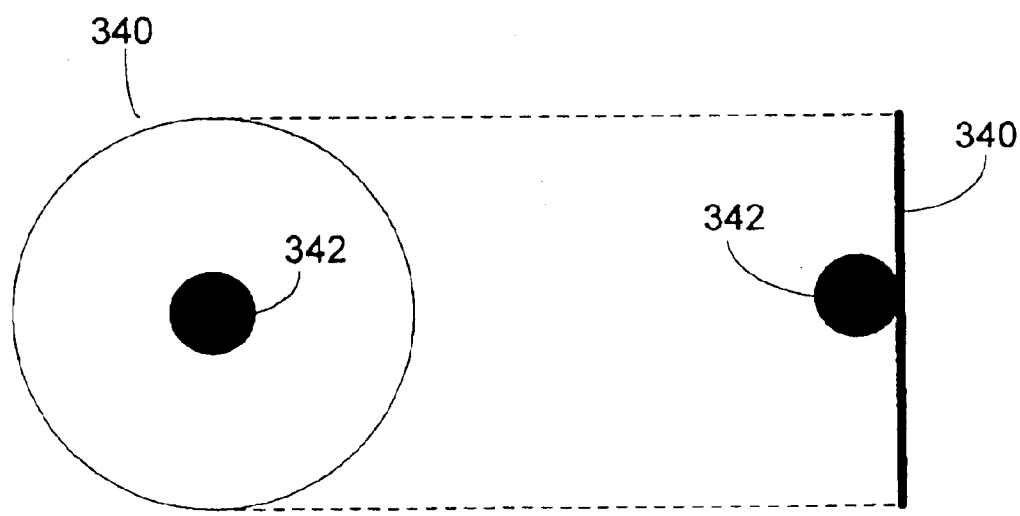
FIG. 7 shows a type of tie point fitting for use on the face of a patient.

In one operating approach, a clinician bonds tie points to teeth using a fitting such as that of FIG. 6. Clinician then takes one or more impressions of the patient during a records session. The impressions are used after completion of the records session to generate an appliance and coordinates of the teeth and tie points are generated during the manufacturing of the appliance. The clinician then takes stereo X-ray images and 3D images of the patient. Alternatively, in lieu of the stereo X-ray images, conventional biplanar (frontal and lateral) X-ray images generated from only one emitter can be utilized, provided that the X-ray system is calibrated and that the dental and facial tie points are unambiguously identifiable on the lateral and frontal X-ray images. In such an application, however, 3D location of anatomical structures other than those lying in the sagittal plane cannot be effected.

In a second approach, the clinician takes appropriate impressions. An appliance is then created with tie points embedded at known locations with respect to the teeth. The appliance containing the tie points is provided to the clinician who positions it in the patient's mouth. X-ray and 3D facial images are then captured, as discussed above.

Figure 3C:
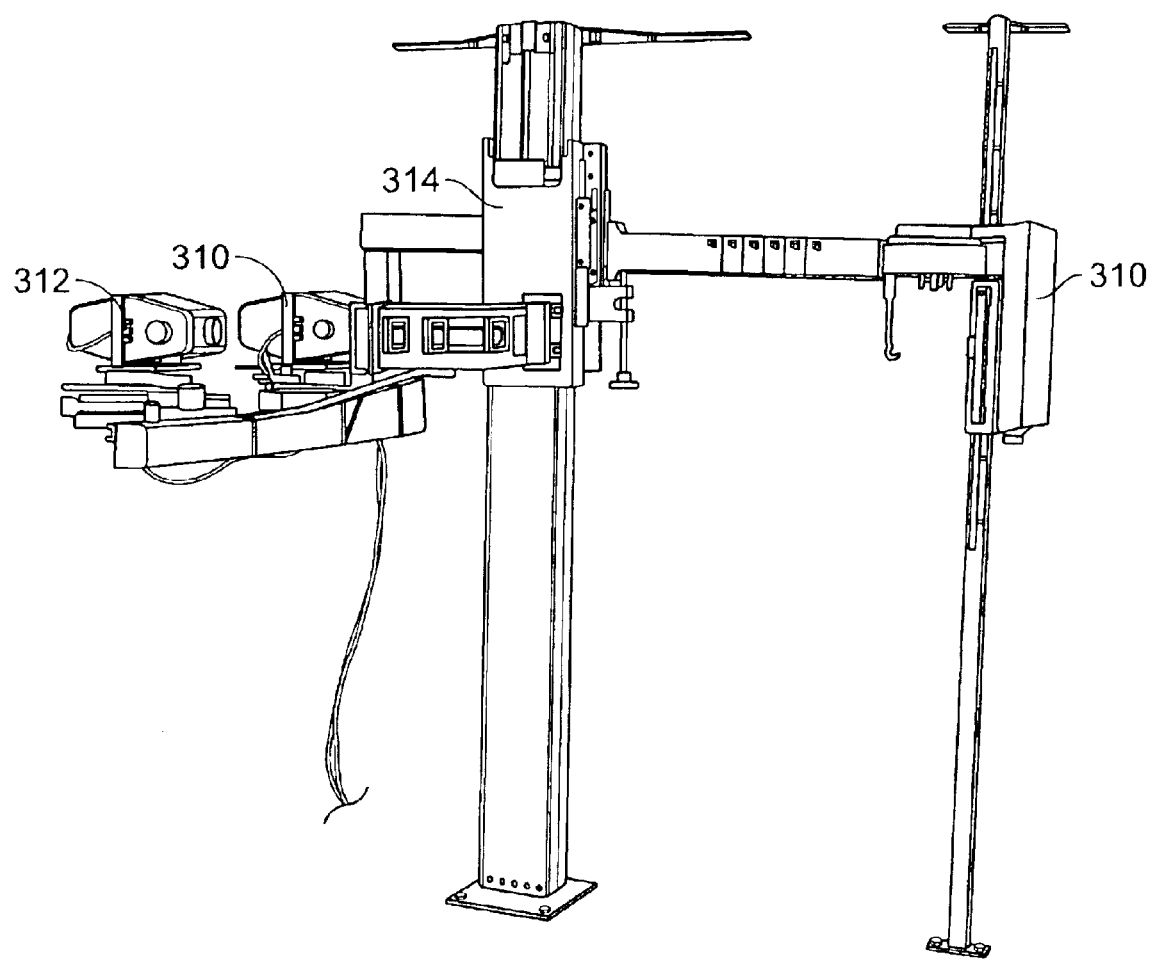

FIGS. 3A, 3B and 3C illustrate top view, side view and perspective view of an embodiment of a stereo X-ray machine. The stereo X-ray machine has two emitters 310–312 that are mounted on a horizontal bar. In this embodiment, the emitter 312 is positioned 18 inches from the emitter 310. The emitter 310 is positioned 60 inches directly from a patient 316. The patient 316 is positioned in a cephalostat (not shown) approximately six inches in front of a cassette carrier 318 (FIGS. 5A–5B) which defines the datum plane. The emitters 310–312 and the cassette carrier are vertically supported by a support stand 314. The emitter 310, the cephalostat and the cassette carrier are offset from the stand 314 by about twelve inches. The stand 314 allows the X-ray equipment to be adjusted to the height of the patient 316.

This embodiment includes a rigid rectangular structure with twin HRT1 General Electric X-ray emitters 310–312 mounted at one end. At the opposite end of the stereo X-ray imaging system, beyond the patient's head is a machined cassette holder defining the datum plane 319. The emitters 310–312 and the carrier or cassette holder 318 taken together constitute the "cameras" of the stereo system. The relationship between the cassette holder 318 and both X-ray emitters 310–312 is known through previous use of a calibration device. The calibration process consists of imaging a calibration cage with three planes of precisely known radiopaque targets. Using a simultaneous least squares adjustment ("bundle adjustment"), the 3D locations of the X-ray emitters are determined.

The mathematical calculation of the 3D positions of the tie points and anatomical structures on the stereo X-ray images depend upon having accurate and precise information on the physical relationships between the focal spots of the two entities (310 and 312) and the surface of the X-ray film or its digital equivalent located in the cassette carrier at 318. The information needed includes: (1) the distance between the two focal spots 310 and 312, measured parallel to the surface of the film in the cassette carrier; (2) the perpendicular distance between each focal spot and the plane of the film surface, and (3) the precise location of the cassette within the cassette carrier for each exposure. This location differs slightly for different projections as may be seen by examining the X-ray intersections in FIG. 3A. To obtain this data, a calibrated array, the cassette carrier previous mentioned, and an "auxiliary calibration checking frame."

FIGS. 4A–4D illustrate an exemplary calibration array 500. An imageable structure of known dimensions is placed in a location from which it can be X-rayed. The structure consists of a radiolucent framework upon which are mounted a number of radiopaque points whose three space locations with respect to each other are known with accuracy and precision. In the simplified illustrated case there are four perpendicular radiolucent plastic rods 502, 504, 506 and 508 at the top and bottom of which the radiopaque points are mounted perpendicular to each other. When the X-ray image is exposed, the shadow points 503, 505, 507 and 509 of the top of the rods 502, 504, 506 and 508 will be cast upon the film surface, radially displaced with respect to the original three space position of the rod top point. A line drawn in three space which passes through both any rod top point and the image of that point on the X-ray film will also pass back along the path of the ray which erected the image through the focal spot from which the ray originated. This principle is shown in photogrammetry as the principle of resection. Since the same principle applies to all four rods, a series of lines passing through an X-ray focal spot (corresponding to point 310 or 312 of FIG. 3A) may be generated, the intersection of any two of which would identify the focal spot uniquely if the measurements were without error. Since there is always error, redundancy is added in this implementation by the use of four rods rather than two.

By repeating exposures for both X-ray sources, (the equivalents of 310 and 312), the distance from each X-ray source to the film plane can be computed. Next, a point 520 on the film plane at which the perpendicular ray strikes the point is identified. This point is called the "principle point" and the distance between the principle points of both X-ray images in the precise measurement of the distance between the focal spots of the two X-ray sources measured parallel to the film surface.

To locate the principle point for each X-ray source, a line is drawn in the plane of the film passing through the images of each rod top point and its rod own bottom point. Information from two rods can be used in the absence of measurement error and the redundant information arising from the use of four rods strengthens the calculations in the presence of error. At this point, the distance from each X-ray source to the film plane, the point of contacts on the film plane of the principle ray from each source, and the distance between the two X-ray sources are known.

Figure 4A:
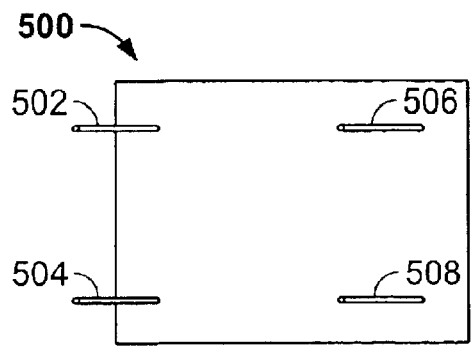
FIGS. 4A–4F illustrate an exemplary calibration array.
Figure 4B:
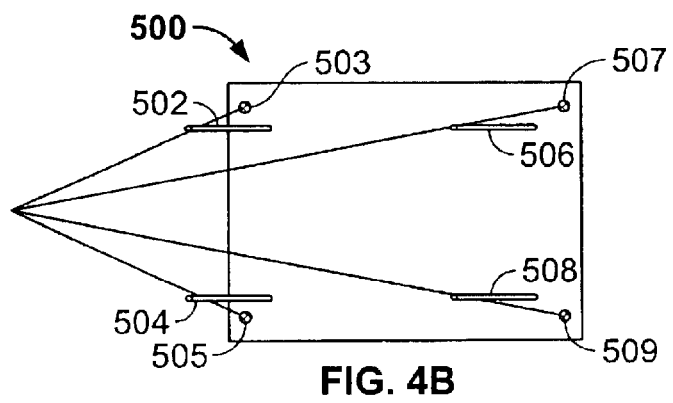
Figure 4C:
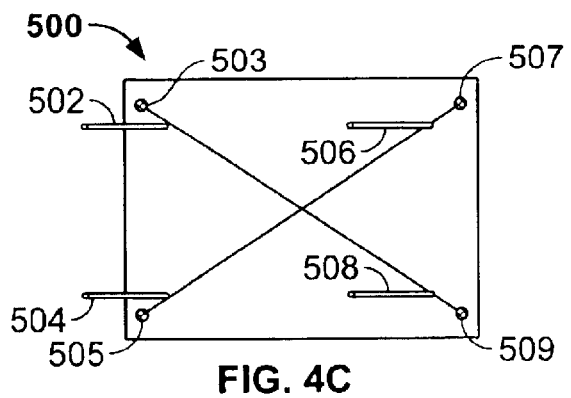
Figure 4D:
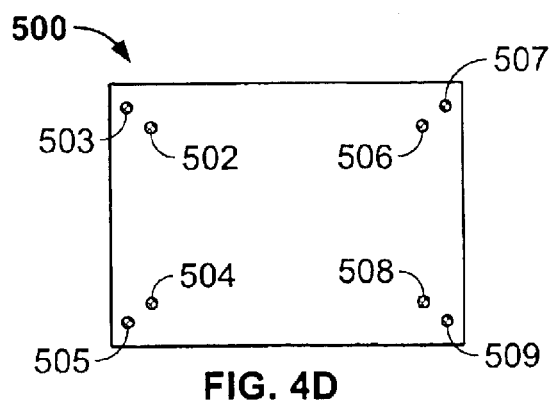
Figure 4E:
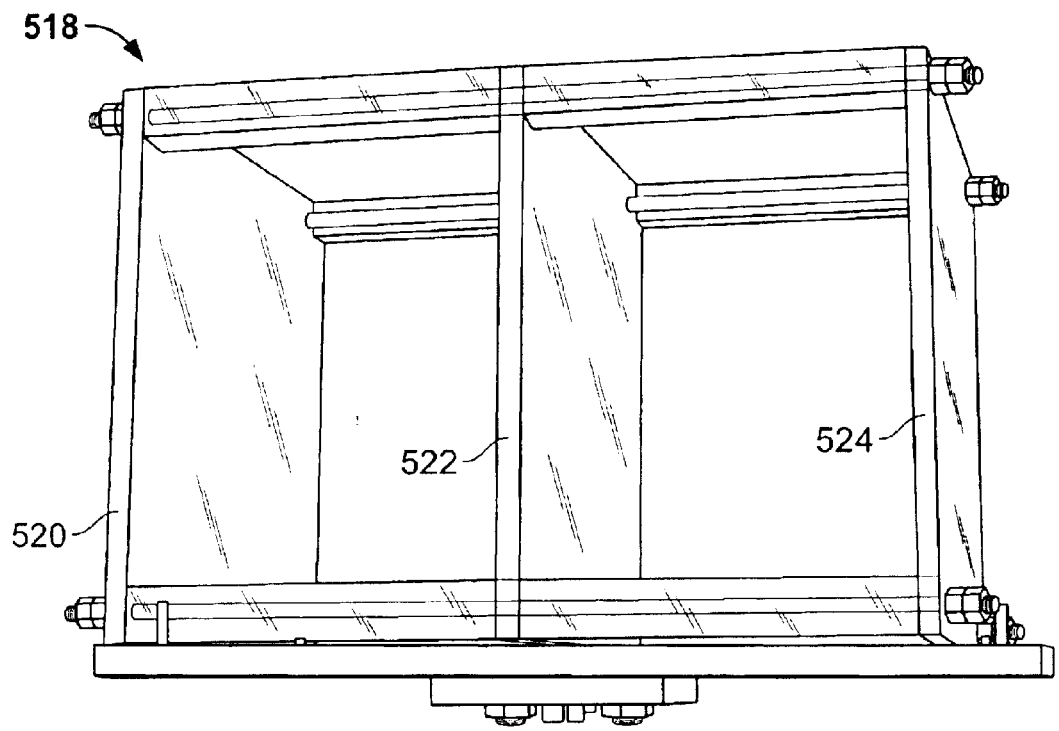
Figure 4F:
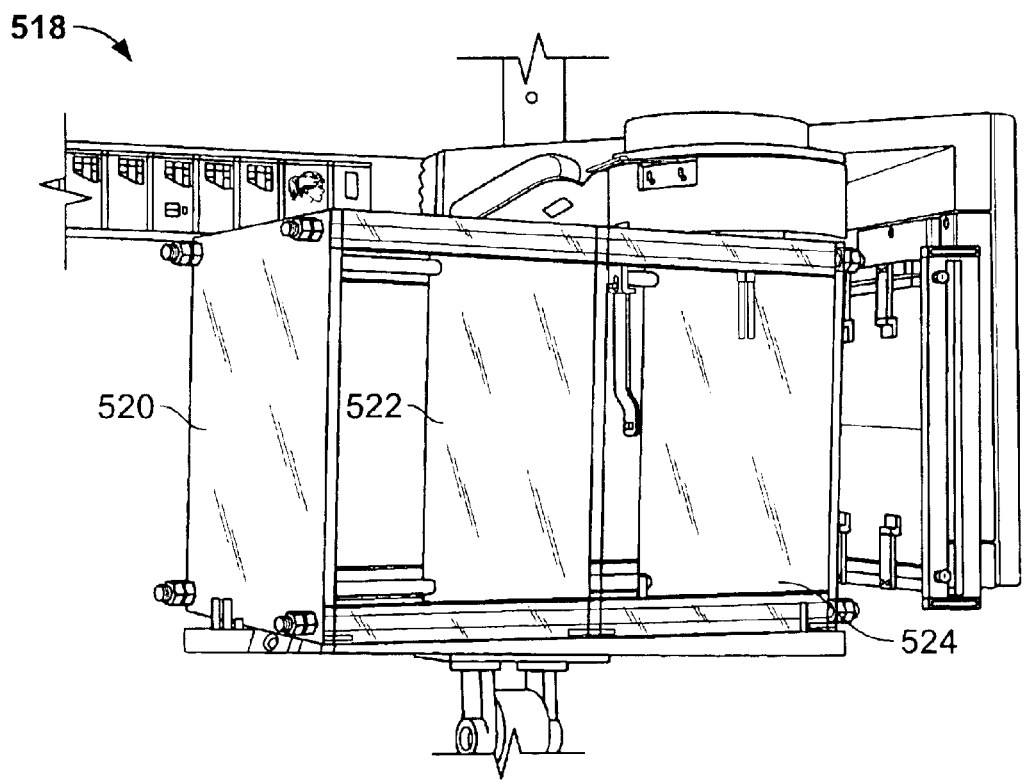

In certain cases, it is impractical to use the system of four perpendicular rods surrounding the patient's head because of physical clashes with the cephalostat that is required for the control of head orientation in object space. For this reason, another exemplary calibration device 518 is shown in FIGS. 4E and 4F. The second embodiment consists of 3 plastic planes 520–524 assembled in parallel layers, successively separated from each other by intervals of a known value, in one embodiment 9.5 inches. This device is positioned between the X-ray sources and the film plane, as near as possible to it. In this embodiment, the plane of the device nearest the film plane has nine radiopaque markers in carefully measured locations; the other two planes have four markers each. While the principle of measurement is still resection, the redundancy of this calibration device avoids the need to orient it with great precision with respect to the film plane. The approximate precision in measuring the principal distance with this apparatus is in the one to three millimeter range. The distance between the X-ray emitters can be measured with one millimeter.

The next task is to obtain precise information about the precise orientation of the film cassette with respect to X-ray emitters. For this purpose, a cassette holder 318 (FIGS. 5A–5B) is rigidly attached to X-ray emitters or sources 310 and 312. The holder 318 has on its surface a set of precisely positioned radiopaque fiducial points (325 being typical) whose precise coordinates are known through direct measurements. These fiducials, in sets of at least four are imaged on the film surface during exposure, thus identifying the precise position of each film with respect to its X-ray source.

Since the control array cannot be maintained in position all the time, a slightly lower order auxiliary calibration checking frame is supplied. This device (not shown) consists of a smaller number of radiopaque spheres mounted on a plastic cone or box in known positions which can be periodically fastened to a cassette positioned within the cassette holder. While it is not sufficiently redundant for use as a calibration array, it is powerful enough when used periodically to check the robustness of calibration achieved using the full calibration array.

The sequence of steps in the operation of the stereoscopic X-ray system is as follows:

1. The subject's head is positioned within the object space, secured in a head holder or cephalostat to minimize movement between exposures.
2. A cassette containing an unexposed X-ray imaging medium (film or digital medium) is positioned in the cassette carrier 318.
3. The X-ray emitter located at a first station is fired, exposing the film or a digital image capture medium.
4. The first cassette is removed and replaced with a new cassette containing a new unexposed film or digital image capture screen medium.
5. The X-ray emitter located at a second station is fired exposing the film.

After producing the stereopair of lateral skull films, the patient and the cephalostat are next rotated 90 degrees such that the patient faces the cassette carrier 318. Two more films are exposed from the first and second stations. These constitute a frontal X-ray stereopair. The film pairs are processed and examined by a monocular analytic method in which a person examines the two images sequentially and marks the locations of the cassette holder fiducial points, the tie points, and one or more sets of anatomical landmarks. The location of these structures on the X-ray images can be done manually or by using suitable computer programs.

Software is then used to examine the tracings for each film as a unit of information. If duplicate tracings have been made, the software rotates, translates and rescales the multiple tracings for each X-ray image to a least squares best fit upon the directly measured known X and Y coordinates of the fiducial points on the datum plane. The set of coordinate values for all landmarks of each film is stored as a block. The coordinates of the principal point of each film and of the fiducial points on the datum plane are added to the set of coordinate values for the X-ray image.

The coordinate files for the two films of each stereopair are now used to produce a three dimensional map in the following manner. The file for the film from second camera station (the offset film) is rotated and translated such that its four registration points are best fit upon the registration points of the film from the first camera station (the centered film). The X parallax of each point in the system may now readily be computed as the ΔX between any landmark on the "centered" film and its conjugate on the "offset" film, and the altitude of the landmark is computed automatically using standard photogrammetric equations. In addition, the Y parallax for each landmark and registration point is computed as measure of the degree to which the same physical structure was actually identified on both films of the stereopair. More information on the transformations is described in Elements of Photogrammetry, Paul R Wolf, McGraw-Hill (1974). Systematic Y parallax deviation for anatomical landmarks which are significantly greater than those for the fiducials are indicators of patient movement between the exposure of the two images of the stereopair.

In one embodiment, the raw data acquisition module receives 3D facial data from a 3D camera such as the Venus3D camera available from 3DMetrics of Petaluma, Calif. The 3DMetrics camera uses a 3D Flash light projector and a conventional digital camera. The 3D Flash light projector projects a color-coded white light pattern onto an object, the digital camera takes an image of the object, then the data is transmitted to a computer which performs a crosstalk-free-color-decoding operation. The 2D data is then converted into a 3D image. In this manner, the 3D camera or imaging system enables a single regular digital camera to take a 3D image with only one shot and does not require any additional mechanical scanning, laser light source, or additional shots. The 3D data generated by the 3D camera is then scanned for the location of tie points. In one embodiment, the tie points are manually identified by a person. Other embodiments would provide automatic detection of the tie points.

Figure 5A:
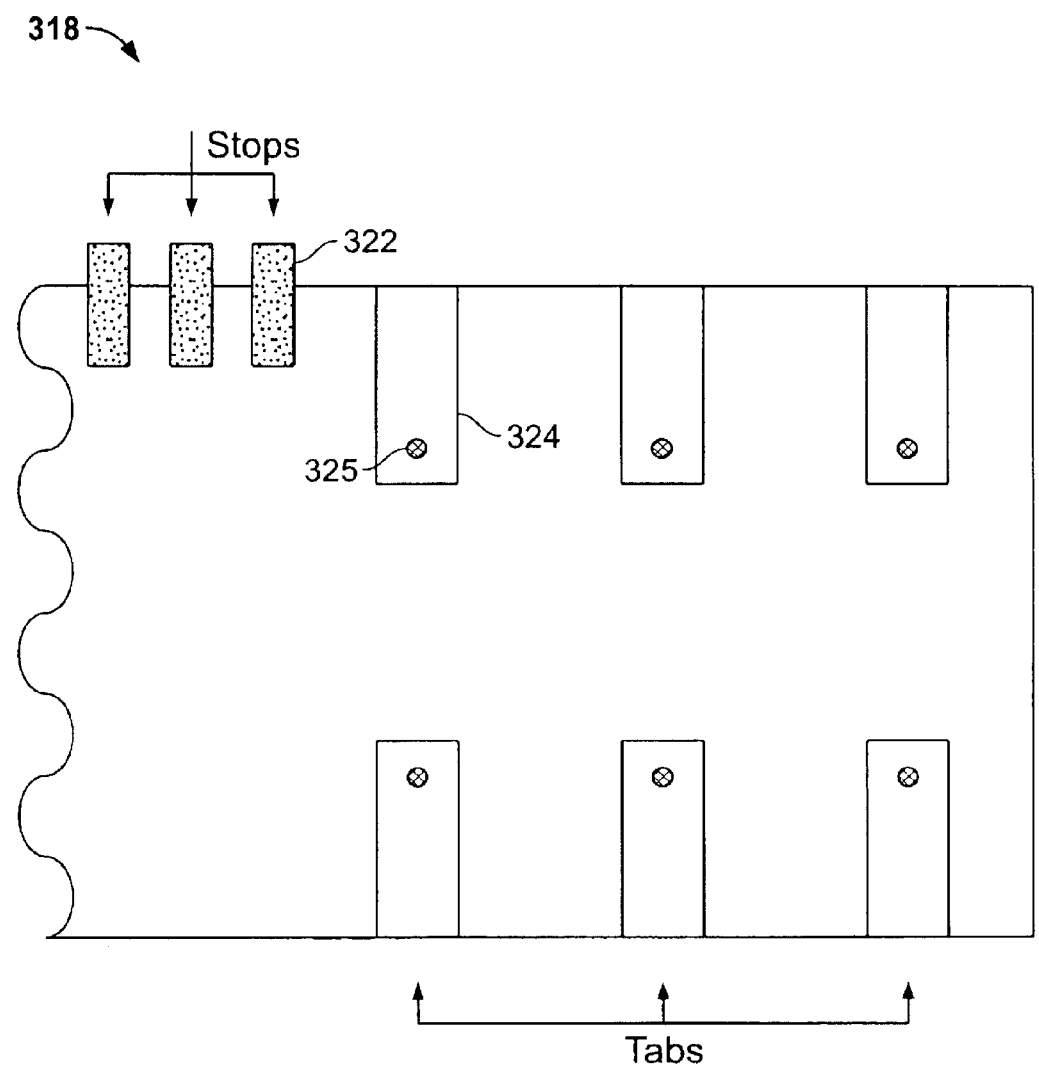

Referring now to FIGS. 5A–5B, a cassette carrier 318 is shown. The cassette carrier has a plurality of tabs or fiducial markers 324 and a plurality of stop points 322. An X-ray cassette is inserted into the cassette carrier and slid into position behind the tabs 324. The tabs 324 are radiolucent and carry radiopaque fiducial control points similar in size to the tie points. However, they differ from tie points in that their exact spatial location with respect to the X-ray tubes 310 and 312 are previously shown through prior calibration. The stop points 322 are adjustable to limit the lateral traversal of the cassette at various desired positions.

FIG. 6 shows two views of a tie point fitting used with for use with a direct bonding onto the teeth of a patient. The tie point fitting has a plastic carrier 332. Mounted on top of the plastic carrier 332 is a radio opaque tie point 330. As shown in the side view and the edge view, the plastic carrier 332 has serrations at a bottom end to facilitate mounting of the tie points 330 onto a tooth of a patient using a suitable glue or bonding system.

FIG. 7 shows a tie point fitting for use on the face of a patient. A tie point 342 is positioned on top of a paper or adhesive tape carrier 340. The carrier 340 has an adhesive backing that attaches the tie point to the face of the patient.

Figure 8A:
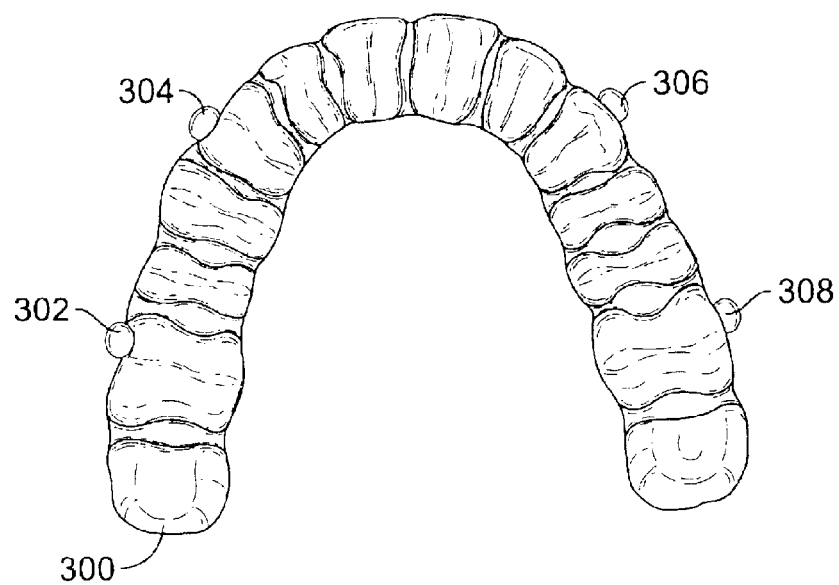
FIGS. 8A and 8B illustrate radiographic markers that are embedded in an appliance.
Figure 8B:
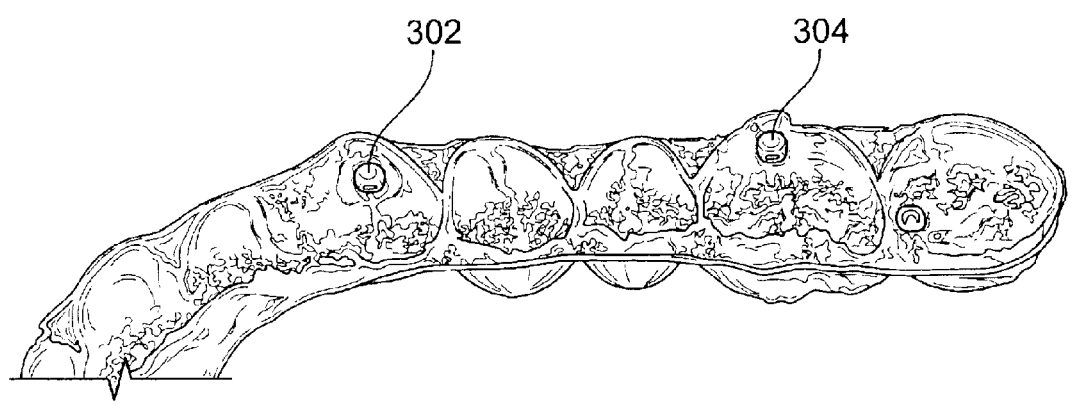

Next, appliances with radiographic markers will be discussed. In one implementation, radiographic markers are embedded in an appliance 300, shown in FIGS. 8A and 8B. The appliance 300 is a polymeric shell having a cavity shaped to receive teeth. The polymeric shell typically fits over all teeth present in the upper or lower jaw. The polymeric appliance 300 is preferably formed from a thin sheet of a suitable elastomeric polymeric, such as Tru-Tain 0.03 in thermal forming dental material, marketed by Tru-Tain Plastics, Rochester, Minn. 55902. The appliance 300 has four radiopaque metal pins 302, 304, 306 and 308. In one embodiment, the radiographic markers or tie points are stainless steel spheres that are ³⁄₃₂" in diameter, grade 100 material with sphericity within 0.0001 inch and with a hardness rating of Rockwell C 39. Only three tie points are sufficient to determine a common plane for merging two 3D maps if they are located perfectly. However some redundancy is desirable and so the present system employs a minimum of four. Although four tie points are shown in FIGS. 8A–8B, six tie points can be used in the event that the patient has fillings that in some way obscure some of the tie points in the X-ray images.

One procedure for creating the appliance 300 with the radiographic tie points 302–308 is discussed next. First, a dental professional takes one or more PVS impressions and a wax bite for measuring inter-arch relationship. The impressions are used to generate one or more models, which are then scanned. The dental professional then sets up a bite registration of both arches, and tooth-attachments are mounted onto the desired teeth which is exactly the same size and shape of the actual tie points 302–308. In one embodiment, the attachments are mounted on three teeth in each quadrant (canines, first molars and second molars for a total of twelve attachments in both arches. Aligners are then fabricated with sufficient spaces for retaining the tie points 302–308. The tie points 302–308 are positioned onto the spaces, and a thin film of unfilled composite adhesive is applied to secure the tie points 302–308. Next, the dental professional opens the occlusal surface of aligners to establish contact between the opposing maxilla and mandible casts. Further, the dental professional can polish the appliance 300 to make it more comfortable to wear.

Figure 9:
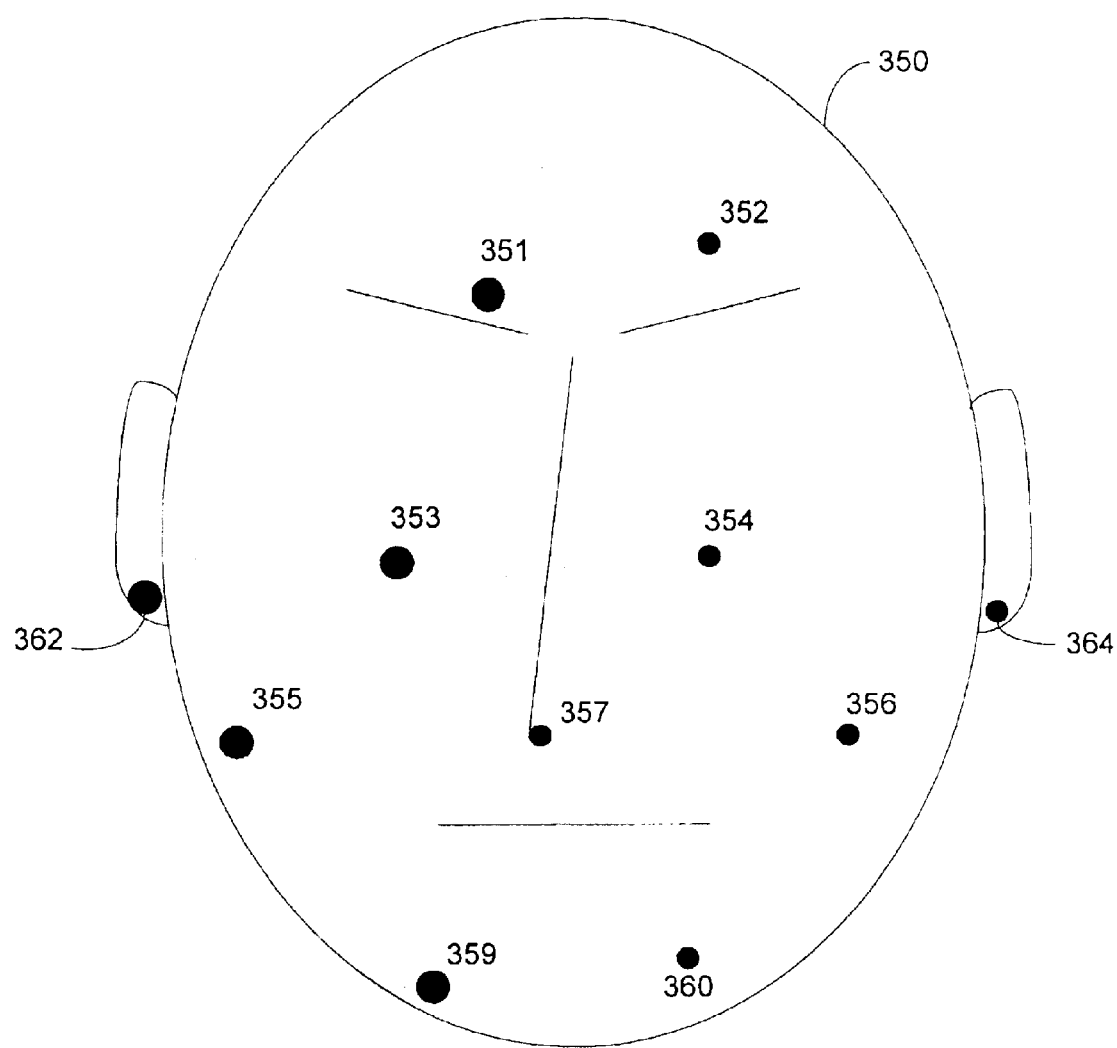
FIG. 9 illustrates an exemplary mounting of a number of tie points on a subject's face.

FIG. 9 illustrates an exemplary mounting of the tie points on a face 350. Points 351 and 352 are located on the forehead above the eyebrows and are called supercilliary points. Point 353 and 354 are the zygomatic points and are located on the anterior aspect of the cheekbone. Points 355 and 356 are the gonial tie points and are located at the angle of the lower jaw. Point 357 is the nasal tie point and is located on the tip of the nose. Points 359 and 360 are the anterior jaw tie points one being located on each side of the chin. Points 362 and 364 are the ear tie points located just above the earlobe. In general, at least 3 tie points must be visible on at least two images of any set of averages to be used for merging map components. Further, the tie points should surround the biological region of interest so that measurement to the biological point can be interpolated.

Additionally, the geometry is more efficient if no more than 2 points are situated along a common line.

In order to avoid the possibility that images of the tie points on the right and the left sides of the face are confused when locating them on lateral X-ray images, the facial tie points on the side of the face nearer to the X-ray emitters 310 and 312 are slightly larger and are positioned slightly lower on the face than are the facial tie points on the side of the face nearer to the cassette carrier 318. Similarly, to avoid errors, the tie points on the upper teeth are a slightly different size from the tie points on the lower teeth. The information in the tie points alone is itself sufficient for the construction of an integrated three-dimensional craniofacial image map without any specialist intervention or time commitment.

In another implementation, the procedures for the 3D mapping operation are as follows:
(1) Conventional upper and lower impressions are taken and conventional dental casts are poured and trimmed.
(2) Without damaging the casts, thin cold cure acrylic upper and lower appliances are fabricated in such a way as to be stably positionable in the mouth without occlusal interference.
(3) Three or more radiopaque tie points are imbedded into each acrylic appliance with the top points visible at the surface. These are the cast control tie points. (Note: steps 4–7 are performed during the same visit.)
(4) The acrylic appliances are placed in the subject's mouth.
(5) Three or more radiopaque tie points are fixed to the lateral and frontal aspects of the patient's face. These are the facial control tie points.
(6) The patient is positioned in the object space of the stereo X-ray system as described above and the lateral and frontal X-ray stereopairs are taken as described.
(7) The patient is positioned in the object space of the facial photographic system and lateral and frontal photographic stereopairs are taken.
(8) The upper and lower acrylic appliances are returned to their respective casts and the casts are individually stereophotographed in appropriate positions.
(9) (Optional) If checks on bite relationship are desired, the appliances may be returned to the mouth and a wax check bite registration may be made. The appliances and the wax bite are removed from the mouth, fastened together and stereo X-rayed. The relationship of the tie points on this X-ray pair constitutes a mathematically applicable control on the correctness of the bite relationship during the taking of the lateral and frontal stereo X-ray pairs.
(10) Appropriate tracings are made of the X-ray and photographic stereopair. Note that each tie point must be located both on the photographs and on the X-ray images.
(11) The tracing data is reduced to coordinate form.

The two dimensional coordinates of all points can be used to produce a single integrated dimensional craniofacial map.
(13) Stored maps from different time points or different subjects may be compared as desired.

Additional supplementations of the stereo X-ray system have been used in prosthetic dentistry (R. Bellagamba, F R Brigante, S. Baumrind (1986) *J Prosthetic Dent*. 55:625–28) and in orthopedic surgery for the detection of pseudarthrosis following lumbar fusions (N. Chafetz, S. Baumrind, J E Morris, H K Genant, E L Korn (1985) *Spine* 10–368–75) and for the detection of loosening of femoral prostheses (N. Chafetz, S. Baumrind, W. Murray, H K Genant, E L Kom (1985) *Clinical Orthopedics and Related Research* 210–60–67).

Figure 10:
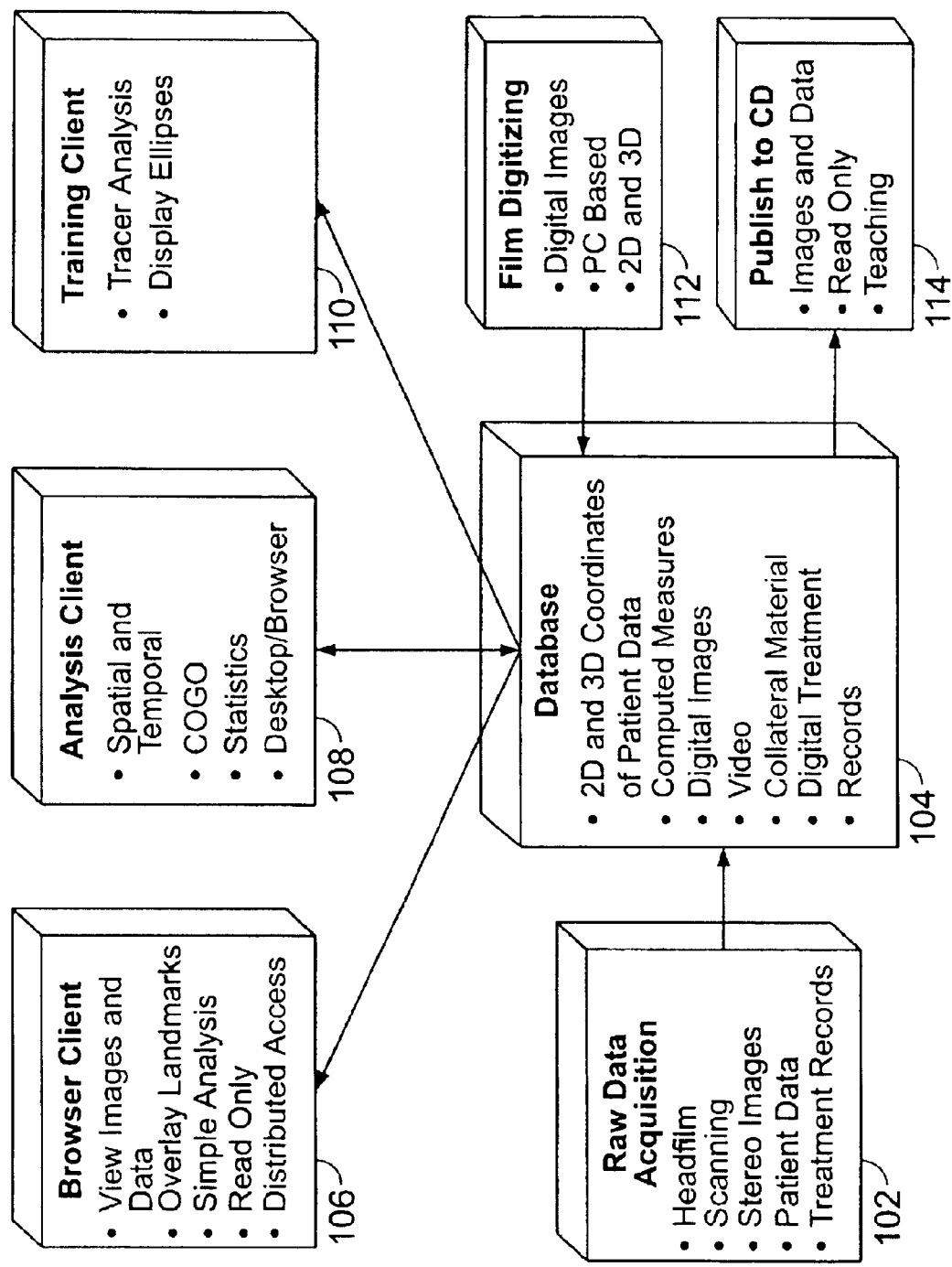
FIG. 10 is a diagram showing a data management system supporting the integration of three-dimensional craniofacial analysis from a combination of data sources.

FIG. 10 shows a data storage and management system for processing integrated three-dimensional craniofacial analysis from a combination of data sources. The system integrates 3D data from stereo cranial X-rays, stereo digital facial images, and digital models of the dentition. The system includes a raw data acquisition module 102. This system acquires patient data including data from headfilm scanning, stereo images, patient data, digital facial images, study cast images, X-ray images and video, collateral material associated with the patient, and treatment records. The output of the raw data acquisition module 102 is provided to a database 104.

The database 104 maintains 2D and 3D coordinates of patient data, computed measures derived from the patient data, digital facial images, study cast images, X-ray images and video, collateral material associated with the patient, and treatment records. The database 104 also receives data from a film digitizing module 112, which extracts 2D and 3D coordinate information from the raw images of the patient. The database 104 can also output data using a publication module 114. The publication module 114 can publish image as well as text data for a variety of applications, including teaching and data sharing.

The database 104 can be accessed using a variety of browsers 106, 108 and 110. The browser client 106 can view images and data. The browser client 106 can overlay landmarks upon request, and perform various analytical operations. The analysis client 108 performs spatial and temporal analysis and other statistical operations, among others. The client 108 contains one or more analytical software tools for analyzing data in the database 104. The training client 110 performs tracer analysis and displays ellipses, among others. The client 110 is a training module for training and calibrating human judges so that they are consistent in identifying points on images. The display ellipses store information relating to acceptable deviations between two judges. As such, the display ellipses improve the quality of the landmark locations on X-ray images and photographs. Thus, the database 104 supports training (calibrating) clinicians and the treating professionals in identifying three-dimensional landmark locations, and integrating information from pairs of X-ray images to yield three-dimensional data and comparing information from multiple time points.

Figure 11:
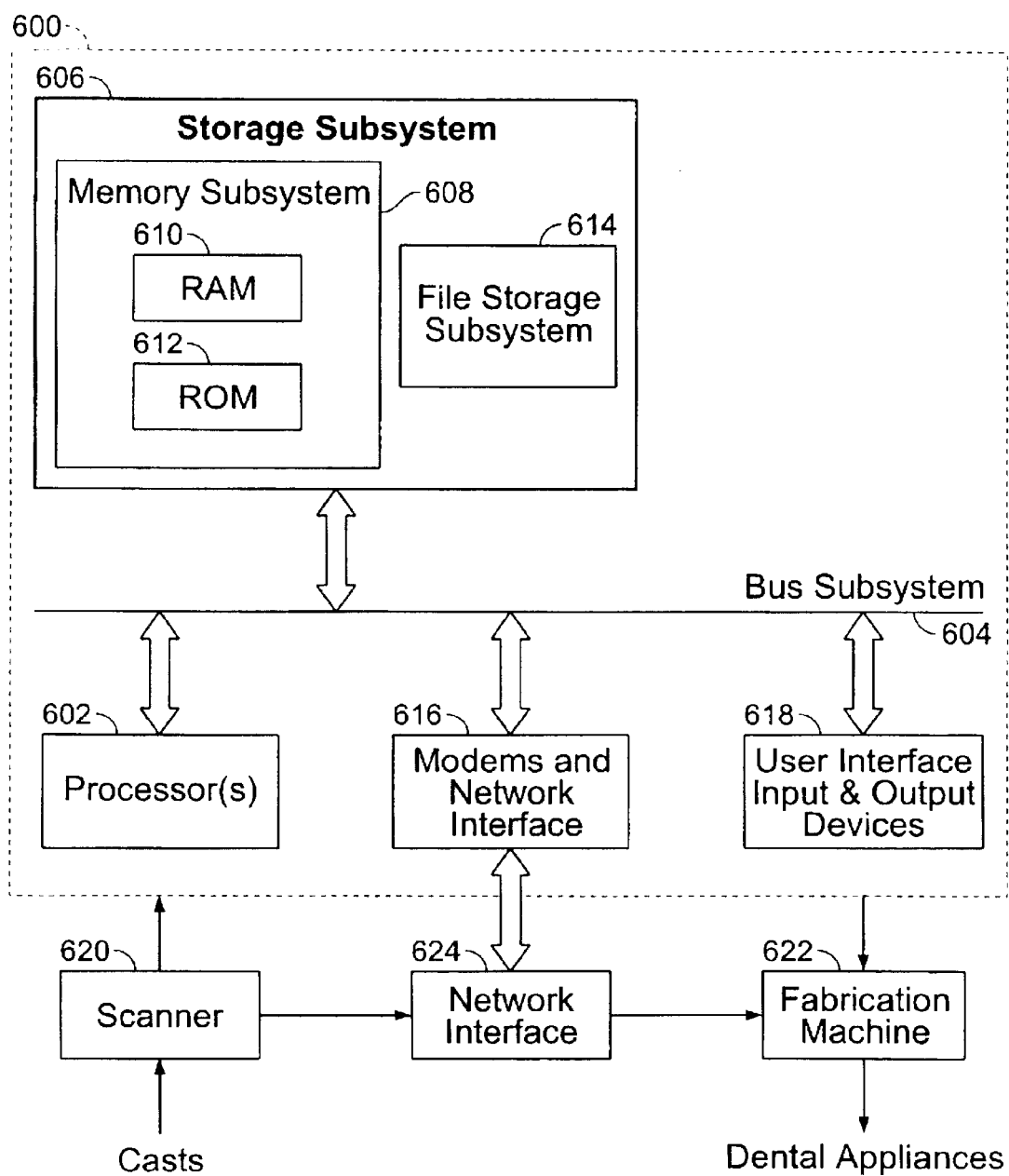
FIG. 11 is a simplified block diagram of a data processing system used to generate an appliance.

FIG. 11 is a simplified block diagram of a data processing system 600 that may be used to generate the appliance 300 of FIGS. 8A–8B. The data processing system 600 typically includes at least one processor 602 that communicates with a number of peripheral devices via bus subsystem 604. These peripheral devices typically include a storage subsystem 606 (memory subsystem 608 and file storage subsystem 614), a set of user interface input and output devices 618, and an interface to outside networks 616, including the public switched telephone network. This interface is shown schematically as "Modems and Network Interface" block 616, and is coupled to corresponding interface devices in other data processing systems via communication network interface 624. Data processing system 600 could be a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touchpad, or graphics tablet, or a direct pointing device such as a touchscreen incorporated into the display, or a three dimensional pointing device, such as the gyroscopic pointing device described in U.S. Pat. No. 5,440,326, other types of user interface input devices, such as voice recognition systems, can also be used. User interface output devices typically include a printer and a display subsystem, which includes a display controller and a display device coupled to the controller. The display device may be a cathode ray tube (CRT), a flat-panel device such as a liquid crystal display (LCD), or a projection device. The display subsystem may also provide nonvisual display such as audio output.

Storage subsystem 606 maintains the basic required programming and data constructs. The program modules discussed above are typically stored in storage subsystem 606. Storage subsystem 606 typically comprises memory subsystem 308 and file storage subsystem 614.

Memory subsystem 608 typically includes a number of memories including a main random access memory (RAM) 610 for storage of instructions and data during program execution and a read only memory (ROM) 612 in which fixed instructions are stored. In the case of Macintosh-compatible personal computers the ROM would include portions of the operating system; in the case of IBM-compatible personal computers, this would include the BIOS (basic input/output system).

File storage subsystem 614 provides persistent (non-volatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected via various local-area or wide-area network media, including telephone lines. Similarly, the input devices and display need not be at the same location as the processor, although it is anticipated that personal computers and workstations typically will be used.

Bus subsystem 604 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 620 is responsible for scanning casts of the patient's teeth obtained either from the patient or from an orthodontist and providing the scanned digital data set information to data processing system 600 for further processing. In a distributed environment, scanner 620 may be located at a remote location and communicate scanned digital data set information to data processing system 600 via network interface 624. Fabrication machine 622 fabricates dental appliances based on intermediate and final data set information received from data processing system 600. In a distributed environment, fabrication machine 622 may be located at a remote location and receive data set information from data processing system 600 via network interface 624.

The invention has been described in terms of particular embodiments. Other embodiments are within the scope of the following claims. For example, the three-dimensional scanning techniques described above may be used to analyze material characteristics, such as shrinkage and expansion, of the materials that form the tooth castings and the aligners. Also, the 3D tooth models and the graphical interface described above may be used to assist clinicians that treat patients with conventional braces or other conventional orthodontic appliances, in which case the constraints applied to tooth movement would be modified accordingly.

What is claimed is:

1. A method for integrating anatomical information from a plurality of sources of information, comprising:

receiving two or more three dimensional (3D) anatomical maps sharing a common plane specified by three or more marker points common to the two or more maps;

placing one or more marker points on one or more teeth;

generating a digital model of the teeth with the marker points; and aligning the two or more 3D anatomical maps and the digital teeth model using the marker points.

2. The method of claim 1, wherein the anatomical information is stereo craniofacial data.

3. The method of claim 1, wherein one of the anatomical map is an X-ray map.

4. The method of claim 3, wherein the X-ray map is generated using correlated points on X-ray pairs and using y-parallax measurements.

5. The method of claim 3, wherein the X-ray information is stereo.

6. The method of claim 3, further comprising calibrating one or more X-ray sources.

7. The method of claim 6, further comprising determining a principal distance from an X-ray source to a film plane.

8. The method of claim 6, further comprising characterizing internal dimensions of the one or more X-ray sources by locating an X-ray film relative to an X-ray source.

9. The method of claim 1, wherein one of the anatomical map is a 3D image map.

10. The method of claim 1, wherein the placing of the markers further comprises wearing a dental appliance with one or more marker points.

11. The method of claim 1, wherein each marker is a tie point.

12. The method of claim 1, wherein the aligning uses discrete anatomical landmark information.

13. The method of claim 1, further comprising displaying the aligned maps as an integrated 3D anatomical model.

14. A system, comprising:

an appliance with one or more teeth markers embedded therein wherein each marker is a tie point;

an X-ray camera receiving X-ray information with X-ray marker information;

a three-dimensional digital camera receiving three-dimensional anatomical information with anatomical marker information;

a dental scanner to generate a three-dimensional teeth model with teeth marker information; and a computer to align the X-ray information, 3D anatomical information, and the 3D teeth model using the marker information.

* * * * *